United States Patent [19]

Rimler et al.

[11] 3,980,523

[45] Sept. 14, 1976

[54] METHOD OF PROPAGATING MICROORGANISMS

[76] Inventors: Richard B. Rimler, 200 Kings Circle; Richard B. Davis, Rte. 3, Box 321 C, both of Athens, Ga. 30601

[22] Filed: Mar. 14, 1975

[21] Appl. No.: 558,457

[52] U.S. Cl. ............................ 195/96; 195/100; 195/102
[51] Int. Cl.² ................. C12K 5/00; C12B 3/14; C12B 1/08
[58] Field of Search ............. 195/96, 100, 99, 101, 195/102, 103, 114, 28 N

[56] References Cited
UNITED STATES PATENTS

| | | | |
|---|---|---|---|
| 3,445,339 | 5/1969 | Controni et al. | 195/100 X |
| 3,649,460 | 3/1972 | Controni et al. | 195/100 |
| 3,705,080 | 12/1972 | Nakaynma | 195/114 X |
| 3,741,874 | 6/1973 | Gordon | 195/102 |

OTHER PUBLICATIONS

Matsumoto, et al., "A Broth Bacterin Against Infectious Coryza: I Immunogenicity of Various Preparations," *Chem. Abstracts,* vol. 74, p. 318, Abs. No. 138556v, (1971).

Holt, "The Growth-factor Requirements of Haemophilus Influenzae", J. Gen. Microbiol., (1961), vol. 27 pp. 317-322.
Breed et al., *Bergey's Manual of Determinative Bacteriology,* The Williams and Wilkins Co., 1957, 7th Ed. pp. 406-409.
Frobisher, *Fundamentals of Microbiology,* W. B. Saunders Co., Philadelphia, London, Toronto, 8th Ed., pp. 451-453.
Page, "Haemophilus Infections in Chickens. I. Characteristics of 12 Haemophilus Isolates Recoverd from Diseased Chickens," *Amer. Journal Vet. Research,* vol. 23, pp. 85-94 (1962).
Biberstein et al., "Action of Haemophilus Culture on δ-Aminoleuulinic Acid", *J. Bacteriology,* vol. 86, pp. 814-819 (1963).

*Primary Examiner*—A. Louis Monacell
*Assistant Examiner*—Thomas G. Wiseman
*Attorney, Agent, or Firm*—Wellington M. Manning, Jr.

[57] ABSTRACT

A method of propagating the *Haemophilus gallinarum* organism utilizing an aqueous growth medium which produces greater than $10^8$ colony forming units per milliliter. The product in this concentration is useful as an immunologic agent effective against infectious coryza in fowl.

10 Claims, No Drawings

METHOD OF PROPAGATING MICROORGANISMS

BACKGROUND OF THE INVENTION

1. Field of the Invention

This invention relates to an improved process and growth medium for propagating *Haemophilus gallinarum*, with the object of providing a practical immunizing agent for infectious coryza. Infectious coryza has long been a major disease problem for poultry flocks, and particularly for laying chicken flocks. Although infected chickens normally recover within a few weeks, the disease often is complicated by other infections, in which cases chronic respiratory disorders may persist for months, with resultant economic losses. The disease is particularly troublesome in a continuous laying operation with different age groups of birds, and with operations conducted near another flock which might transmit the disease.

Infectious coryza is an acute respiratory disease of chickens caused by *Haemophilus gallinarum*. The disease manifests as severe swelling of the frontal sinus, and can lead to infection of the airsac and generalized airsaculitus. Sometimes chronic secondary infections develop which necessitate culling.

2. Description of the Prior Art

Many attempts have been made to control infectious coryza through such methods as isolation rearing, yearly disposal of laying flocks, and, in some cases, complete depopulation. Such efforts have provided some benefits, but in most cases the disease has reappeared.

It was observed that chickens that had survived an attack of infectious coryza developed a resistance or immunity to reinfection. This observation led to the belief that a controlled infection with a live virulent culture of *Haemophilus gallinarum* administered at the proper time would produce good immunity with a minimum of losses from complicating diseases. This method is not a completely satisfactory solution to the infectious coryza problem because even when the disease is given to young birds before they reach laying age there are still losses due to culls.

More recently, attempts have been made to control infectious coryza with inactivated bacterins prepared from cultured *Haemophilus gallinarum*. One such bacterin is described in Avian Diseases, 5: 37–47 (1961). Egg-yolk-propagated bacterins as described therein lessened the severity and duration of infectious coryza, and provided benefits against related infections and decreased egg production. This type of bacterin has not been widely accepted because it is not completely effective in preventing egg production losses nor does it protect against certain upper respiratory signs.

Another inactivated bacterin prepared by growth of *Haemophilus gallinarum* in an infusion broth was described in Avian Diseases, 15, 109–117 (1971). The bacterin described therein effectively protects the upper respiratory tract of chickens from infectious coryza. However, while the bacterin prepared from infusion broth has been quite effective, it suffers from the fact that at least $10^8$ colony forming units per milliliter of immunogen is required for effective protection, and the bacterin required concentration by centrifugation or the like in order to provide the minimum effective concentration of $10^8$ CFU/ml.

A general discussion of results of inactivated bacterins for prevention of disease caused by *Haemophilus gallinarum* is found in Avian Diseases, 7: 239–256 (1963).

Ortiz and Yamamoto reported very recently at the XV World Poultry Congress on a procedure for producing a broth propagated bacterin against infectious coryza which did not require concentration. Their procedure, however, requires the use of chicken serum or brain heart infusion broth to obtain the necessary concentration.

Thus, there is a need for a method of propagating *Haemophilus gallinarum* to provide, without the need for addition of serum or infusion broth or subsequent concentration, a product containing at least $10^8$ CFU/ml.

SUMMARY OF THE INVENTION

According to the present invention, a growth medium and a process of propagation of *Haemophilus gallinarum* have been developed which produce greater than $10^8$ CFU/ml. This quantity of organism is sufficient for production of an effective bacterin without the need for concentration after growth of the organism.

The growth medium according to the invention comprises assimilable sources of carbon and nitrogen, and also includes sodium ions and reduced nicotinamide adenine dinucleotide ($NADH_2$). The medium of the invention does not require the use of serum or brain heart infusion broth, thus providing important manufacturing efficiencies.

It is an object of this invention to provide a novel growth medium capable of producing at least $10^8$ CFU/ml of *Haemophilus gallinarum* without the need for serum or infusion broth.

It is a further object to provide a novel process of propagating *Haemophilus gallinarum* which provides a product having at least $10^8$ CFU/ml and having immunogenic activity against infectious coryza.

The above as well as other objects and advantages are obtained by the present invention, as will be apparent from the following detailed description.

DESCRIPTION OF THE PREFERRED EMBODIMENTS

This invention enables the propagation of *Haemophilus gallinarum* such that a concentration greater than $10^8$ CFU/ml, the concentration generally accepted as a minimum for use as an inactivated bacterin, can be obtained without the requirement of centrifugation or other concentrating procedures. The following examples set forth results obtained using a virulent strain isolated from an outbreak of infectious coryza in Florida. Substantially the same growth results have been obtained utilizing strains of *Haemophilus gallinarum* isolated from field flocks located in California, Florida and Georgia. The *Haemophilus gallinarum* organism is wellknown to those skilled in the art, and the isolation or identification thereof do not constitute a part of the invention. The organism is a gram-negative, polar-staining, non-motile bacterium. In 24-hour cultures it appears as short rods or coccobacilli 1–3 microns in length and 0.4–0.8 microns in width, with a tendency for filament formation. This organism undergoes degeneration within 48–60 hours, showing fragments and indefinite forms. Subcultures to fresh medium at this stage will again yield the typical rod-shaped morphology.

Stock cultures of *Haemophilus gallinarum* were stored in egg yolk at −70°C until needed for preparation or starter cultures, at which time the organism was serially passed twice thru eggs in the seventh day of embryonation. At 48 hours with death of the last embryo, infected yolk was collected and streaked onto Casman blood agar plates. The plates were cross-streaked with *Staphylococcus aureus* and incubated in a Gaspak jar equipped with a $CO_2$ generator at 37°C for 24 hours. Colonies of the resultant growth were inoculated into a starter culture tube. This tube and subsequent starter culture tubes contained 20 ml of a culture medium to be described in detail later. The tube was incubated at 37°C for 24 hours under $CO_2$ tension. The resultant growth was checked for purity by gram stain and 0.2 ml was inoculated into each of three additional starter culture tubes. These tubes were incubated under $CO_2$ tension at 37°C for 24 hours to provide the final starter culture for use in making the product.

The novel culture medium in accordance with the invention comprises assimilable sources of carbon and nitrogen and additionally contains as essential ingredients a source of sodium ion (preferably sodium chloride) and reduced nicotinamide adenine dinucleotide.

The amount of sodium ion needed is preferably the amount provided by addition of from 0.5 to 1.5 percent by weight of sodium chloride to the medium, although part of the sodium may come from other ingredients of the medium, such as when a sodium-containing buffer is added. The amount of reduced nicotinamide adenine dinucleotide used is much higher than previously used in growth media, and preferably is from 0.00625 to 0.05 grams per liter of medium.

Growth is enhanced by addition of a buffer, such as about 0.02M of phosphate buffer. Leptospira medium base EMJH (Difco) is a suitable phosphate buffer, and contains a small amount of added thiamine which is also beneficial. An atmosphere containing from 5 to 15 percent carbon dioxide maximizes growth.

The medium is preferably adjusted to a pH of 7.0 to 7.8, optimally 7.5, by addition of 1N NaOH.

The composition of the preferred medium is shown in the following table.

TABLE I

| Ingredient | Amount per Liter |
|---|---|
| Polypeptone | 10.0 g |
| Peptone (Biosate) | 10.0 g |
| Beef Extract Powder | 3.0 g |
| Nicotinamide | 0.05 g |
| Para-aminobenzoic acid | 0.05 g |
| Soluble Starch | 1.0 g |
| Dextrose | 0.5 g |
| Sodium Chloride | 9.0 g |
| Polysorbate (Tween 80) | 1.0 ml |
| Leptospira Medium Base EMJH (Buffer with added thiamine) | 3.0 g |
| Reduced Nicotinamide adenine dinucleotide | 0.05 g |
| Distilled Water | Balanced to 1000 ml |

In the above composition, the polypeptone as is well-known in the art is a combination of hydrolyzates of animal and plant products, and the peptone is a hydrolyzate of yeast and caseine. Both products are readily available, such as from Baltimore Biological Laboratories. The remaining ingredients are each readily available. In the above composition, many of the ingredients listed may be deleted, substituted for or varied as to amount, as will be apparent to those skilled in the art. It is essential, however, to have at least 5.0 grams peptone, at least 0.5 grams dextrose or its equivalent, at least 5.0 grams sodium chloride or equivalent sodium ion source, at least 0.006 grams $NADH_2$ and about 0.005 grams thiamine (provided in the above composition by the Leptospira Medium.)

EXAMPLE I

This example describes the preparation of the preferred culture medium according to the invention. Preparation of 1 liter of final medium is as follows. The ingredients, except for the reduced NAD, which will not stand autoclaving, are added to 976 ml of distilled water and heated to solution, cooled to room temperature, and the pH adjusted to 7.5 with 1N NaOH. Distilled water is added to bring the volume to 996 ml. The medium is then autoclaved in a cotton-plugged flask at 15 psi for 15 minutes. 4 ml of a filter sterilized solution containing 12.5 mg/ml of reduced NAD in distilled water is added aseptically to the cooled flask to complete the preparation of 1 liter of the medium.

Preparation of a starter culture has been previously described. The following Example II describes a static method for propagating *Haemophilus gallinarum* utilizing the culture medium of Example I.

EXAMPLE II

A 500 ml Erhlenmeyer flask containing 250 ml of the culture medium of Example I was used in this example. 10 ml of the medium was aseptically removed and stored at 10°C to serve as a turbidometric standard. The flask was warmed to 37°C, and 2.5 ml of a starter culture inoculum was added aseptically. The flask was placed in an anaerobic jar equipped with a $CO_2$ tension (10 percent $CO_2$ in air) for 18 hours at 37°C. Evaluation of growth of *Haemophilus gallinarum* was by turbidity measurement measured as percent transmittance at 540 µm on a Spectronic 20 spectrophotometer. The measured transmittance was 59%. Growth was also evaluated by making serial 10 fold dilutions in 0.02M phosphate buffered saline (1.0% NaCl) at pH 7.5. Three replicate plates of Casman blood agar were inoculated with 0.05 ml per plate at each dilution. The inoculum was not spread and the plates were allowed to dry. *Staphylococcus aureus* was streaked surrounding the inoculum and the plates were incubated at 37°C for 48 hours under $CO_2$ tension. Colony forming units (CFU) were determined as the average of the number of colonies on the three plates at the readable dilution. This example produced $3.73 \times 10^6$ CFU/ml.

EXAMPLE III

This example illustrates a fermentative method of growing *Haemophilus gallinarum*, as distinguished from the static method of Example II. In this example, a fermenter containing 1990 ml of medium as defined in Example I was warmed to 37°C and inoculated with 20 ml of starter culture as previously defined. A gas mixture of 10 percent $CO_2$ and 90 percent air was bubbled thru the medium at 4 psi for 25 minutes. The fermenter was then closed and incubated with constant stirring at 37°C for 18 hours. The resulting product was determined as in Example II to have a transmittance of 55.5 percent and yielded $6.26 \times 10^8$ CFU/ml.

Purity of growth from Examples II and III was checked by gram stain and culture both aerobically and anaerobically. The morphology of the oganisms for both examples consisted of short to medium rods. Few filamentous forms were observed. The Tween 80 was determined to be a regulator of morphology.

The above examples illustrate that *Haemophilus gallinarum* can be propagated without the need for serum or an infusion of fresh meat as previously required to obtain enough CFU/ml for use as a bacterin without the requirement of concentration.

EXAMPLE IV

The procedure of Example II was repeated using the medium of Example I and a different starter culture of *Haemophilus gallinarum*. The 18 hour incubation yielded $3.03 \times 10^8$ CFU/ml with a transmittance of 60.5 percent. This material was used without concentration to prepare a bacterin. A portion of the broth culture was inactivated using 0.25 percent formalin. A 50 ml portion was mixed into an equal amount of of Freund's incomplete adjuvant using a laboratory blender. A second portion of the broth culture was inactivated but no adjuvant added (aqueous suspension). Sterility of these preparations was checked by culture under aerobic, $CO_2$ tension and anaerobic conditions.

EXAMPLE V

This example illustrates the efficacy of the bacterins prepared in the previous example. White leghorn chickens, 16 weeks old and free of known infectious agents were used. pre-inoculation serum samples were negative for antibody against *Haemophilus gallinarum*, *Mycoplasma gallisepticum* and *Mycoplasma synoviae*. The birds were divided into groups and the bacterins and placebos were injected subcutaneously into the neck at the dorsel midline. Birds receiving the adjuvanted preparation were given 1.0 doses, and those receiving the aqueous suspension were given 0.5 ml doses. The birds in Control Group I were given a 1 ml placebo of formalinized medium in Freund's incomplete adjuvant. Birds in Control Group II were not vaccinated. All groups were challenged by contact exposure to an infected bird introduced into the cage 7 weeks after the initial injection. The birds used for contact exposure were infected by dropping about 0.1 ml of 24 hour infected egg yolk into the eye. The test birds were examined 10 days after exposure for clinical signs of infectious coryza. Table II sets forth the results of the test.

TABLE II

| Group | Bacterin | No. of Doses | No. Birds with Clinical symptoms/No. challenged |
|---|---|---|---|
| I | Placebo | 1 | 7/7 |
| II | None | 0 | 7/7 |
| III | Aqueous | 1 | 5/7 |
| IV | Aqueous | 2 | 6/7 |
| V | Adjuvant | 1 | 1/7 |
| VI | Adjuvant | 2 | 1/7 |

As expected, the adjuvanted bacterin was more effective than the aqueous suspension.

Similar, and in some cases better, results have been obtained using an aluminum hydroxide gel adjuvant, particularly where the broth culture is inactivated with merthiolate rather than formalin.

The preceding detailed description and examples show that when using the medium and process of propagation in accordance with the invention the organism *Haemophilus gallinarum* can be produced at concentrations greater than $10^8$ CFU/ml without the requirement of using serum or infusion broth for growth or using concentration procedures for bacterin preparation. The inactivated bacterins produced according to the invention have been shown to be immunogenic.

Thus, this invention provides important advantages over prior art techniques of propagating *Haemophilus gallinarum*.

We claim:

1. A medium for propagating *Haemophilus gallinarum* comprising assimilable sources of carbon and nitrogen in water, the medium further containing as essential ingredients at least the equivalent of sodium ions provided by 5.0 grams per liter of sodium chloride, and reduced nicotinamide adenine dinucleotide in an amount of at least 0.006 grams, per liter, the medium being characterized further by the absence of serum and meat infusion.

2. A medium as defined in claim 1 wherein the sodium ions are present in an amount equivalent to that provided by addition of from 0.5 to 1.0 percent by weight of sodium chloride per liter of medium, and the reduced nicotinamide adenine dinucleotide is present in an amount of about 0.05 grams per liter of medium.

3. A medium as defined in claim 2 containing, per liter of medium, 10 grams polypeptone; ten grams peptone; 3 grams beef extract powder; 0.05 grams nicotinamide; 0.05 grams para-aminobenzoic acid; 1 gram soluble starch; 0.5 grams dextrose; and 2.3 grams phosphate buffer containing thiamine.

4. A process of propagating *Haemophilus gallinarum* comprising incubating *Haemophilus gallinarum* in a medium comprised of assimilable sources of nitrogen and carbon in water, the medium further containing sodium ions and reduced nicotinamide adenine dinucleotide, the incubation taking place under an atmosphere comprised of 5 to 15 percent carbon dioxide in air until a product containing at least $10^8$ CFU/ml is obtained.

5. The process of claim 4 wherein the atmosphere is 10 percent carbon dioxide and the incubation is for a period of 18 hours at 37°C.

6. A method of producing a bacterin effective against infectious coryza in fowl comprising propagating *Haemophilus gallinarum* in a medium comprising assimilable sources of nitrogen and carbon in water, the medium being characterized by the absence of serum or meat infusion and further containing sodium ions and reduced nicotinamide adenine dinucleotide, until a product containing at least $10^8$ CFU/ml is obtained, and then inactivating the product.

7. The method of claim 6 wherein the product is inactivated by addition of merthiolate.

8. The method of claim 6 wherein the product is inactivated by addition of formalin.

9. The method of claim 6 wherein the bacterin is adjuvanted with aluminum hydroxide gel.

10. The method of claim 6 wherein the bacterin is adjuvanted with Freund's incomplete adjuvant.

* * * * *